United States Patent
Ji et al.

(10) Patent No.: US 7,422,866 B2
(45) Date of Patent: Sep. 9, 2008

(54) ON-LINE ENZYMATIC DIGESTION IN SEPARATION-DETECTION METHODS

(75) Inventors: Zhenghua Ji, Wilmington, DE (US); Liangsheng Yang, deceased, late of Wilmington DE (US); by Li Ping Hu, legal representative, Wilmington, DE (US); Barry E. Boyes, Wilmington, DE (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 11/200,708

(22) Filed: Aug. 10, 2005

(65) Prior Publication Data

US 2007/0037242 A1    Feb. 15, 2007

(51) Int. Cl.
*C12Q 1/37* (2006.01)
*C12N 11/00* (2006.01)

(52) U.S. Cl. .................................. 435/23; 435/174
(58) Field of Classification Search ................ None
See application file for complete search history.

(56) References Cited

U.S. PATENT DOCUMENTS

| | | | |
|---|---|---|---|
| 4,266,026 A * | 5/1981 | Breslau ...................... 435/99 |
| 4,448,691 A | 5/1984 | Davis |
| 4,455,381 A | 6/1984 | Magnusson et al. |
| 4,708,800 A | 11/1987 | Ichikawa et al. |
| 5,707,516 A | 1/1998 | Tomizawa et al. |
| 5,736,036 A | 4/1998 | Upchurch et al. |
| 5,885,841 A * | 3/1999 | Higgs et al. ................... 436/89 |
| 6,022,478 A | 2/2000 | Baurmeister et al. |
| 2003/0089605 A1 | 5/2003 | Timperman |
| 2003/0101866 A1 | 6/2003 | Noack |
| 2003/0104350 A1 | 6/2003 | Bomberger et al. |
| 2003/0104483 A1 | 6/2003 | Davidson et al. |
| 2003/0124606 A1 | 7/2003 | Suckau et al. |
| 2003/0129657 A1 | 7/2003 | Decker et al. |
| 2004/0171169 A1 | 9/2004 | Kallury et al. |
| 2005/0239152 A1 * | 10/2005 | Irth et al. ........................ 435/8 |
| 2006/0019399 A1 | 1/2006 | Balgley et al. |

FOREIGN PATENT DOCUMENTS

WO    2002057295    7/2002

OTHER PUBLICATIONS

Trueb et al. Type VI Collagen is Composed of a 200 KD Subunit and Two 140 KD Subunits; The EMBO Journal, vol. 5, No. 11 (1986) pp. 2815-2819.*

Davis, J.C. Kinetics Studies in a Continuous Steady State Hollow Fiber Membrane Enzyme Reactor; Biotechnology and Bioengineering, vol. 16 (1974) pp. 1113-1122.*

Gao, Jun et al., "Integrated Microfluidic System Enabling Protein Digestion, Peptide Separation, and Protein Identification", Anal. Chem. 2001, pp. 2648-2655, vol. 73, No. 11.

Vecchione, Gennaro et al., "A comprehensive on-line digestion-liquid chromatography/mass spectrometry/collision-induced dissociation mass spectrometry approach for the characterization of human fibrinogen", Rapid Commun. Mass Spectrom. 2001, pp. 1383-1390, vol. 15.

EPO Communication dated Nov. 24, 2006 enclosing European Search Report, 4 pp., for EP Application No. 06253811 corresponding to U.S. Appl. No. 11/200,708.

Klein et al.; Journal of Proteome Research; vol. 1(1), 41-45 (2002); "A New Isoelectric Focusing Gel for Two-Dimensional Electrophoresis Constructed in Microporous Hollow Fiber Membranes".

Choudhary et al.; Journal of Proteome Research; VBol. 2(1), 59-67 (2003); "Multiple Enzymatic Digestion for Enhanced Sequence Coverage of Proteins in Complex Proteomic Mixtures Using Capillary LC with Ion Trap MS/MS".

Cooper et al.; Analytical Chemistry; vol. 75(5), 1067-1074 (2003); "Membrane-Based Nanoscale Proteolytic Reactor Enabling Protein Digestion, Peptide Separation, and Protein Identification Using Mass Spectrometry".

Samskog et al.; Journal of Chromatography A; 998:83-91 (2003); "Miniaturized On-Line Proteolysis-Capillary Liquid Chromatography-Mass Spectrometry for Peptide Mapping of Lactate Dehydrogenase".

Slysz et al. Rapid Commun. Mass Spectrom.; 17:1044-1050 (2003); "On-Column Digestion of Proteins in Aqueous-Organic Solvents".

* cited by examiner

*Primary Examiner*—Jon P Weber
*Assistant Examiner*—Paul C. Martin

(57) ABSTRACT

Apparatus and methods are disclosed for digesting a biopolymer in a medium. The medium is disposed adjacent a wall of a hollow element wherein at least a portion of the wall is porous. The medium is then exposed to digestion conditions to cleave the biopolymer into fragments. The fragments are permitted to permeate through the wall of the hollow element. In some embodiments a surface of a wall of the hollow element comprises a digestion agent. In some embodiments the hollow element is disposed within a hollow liner. For analysis and identification purposes, the fragments may be separated and/or detected.

15 Claims, 1 Drawing Sheet

ON-LINE ENZYMATIC DIGESTION IN SEPARATION-DETECTION METHODS

BACKGROUND

Aspects of this invention relate in general to analytic methods involving separation of moiety fragments of interest such as, for example, biopolymer fragments, from other moieties not of interest and from one another and subsequent detection of those moieties. Some aspects of the invention relate in particular to the enzymatic digestion of polypeptides including proteins for the purpose of conducting various analyses of polypeptide fragments.

The clinical diagnostic field has seen a broad expansion in recent years, both as to the variety of materials of interest that may be readily and accurately determined, as well as the methods for the determination. In clinical chemistry these materials may be present in body fluids in concentrations below $10^{-12}$ molar.

In recent years, techniques have been developed for the analysis or determination of organic compounds present in extremely small quantities or at very low concentrations. For example, by combining chromatographic techniques such as liquid chromatography with various detection means such as mass spectrometry, sensitivity in the detection of analytes is enhanced.

The goal of proteomics is to identify and quantitate some or all of the proteins expressed in a cell as a means of addressing the complexity of biological systems. Typically, analysis techniques are employed to generate proteome maps. Proteome maps of normal cells and diseased cells are compared to detect proteins that are up- or down-regulated during physiological responses to disease. These proteins are excised for identification and characterization, using such methods as mass fingerprinting and mass spectrometry.

Column separation-detector techniques such as, e.g., LC/MS or HPLC/MS, are used routinely in proteomic studies as a tool to identify unknown proteins. Enzymatic digestion of model protein is a necessary step in analytic processes such as, for example, the process of peptide mass finger printing (PMF) or peptide mapping by mass spectrometer (MS). The enzymatic digestion of proteins is, of course, well known. It results in the breaking up of the protein molecule into smaller fragments. It is a technique used, for example, in the determination of the amino acid sequence in proteins. The mechanism of such cleavage, and hence the precise constitution of the fragments, varies with the enzyme used and the conditions (e.g. time, temperature and pH) under which the digestion is effected.

At present, enzymatic digestion in many column separation-detector techniques is done mostly off-line. The digestion process is a time consuming task, ranging from two hours to overnight with several manual sample manipulation steps such as desalting, sample purification and concentration and then sample introduction into, for example, LC/MS or HPLC/MS. Perceivably, the digestion process limits the applicability of high-throughput PMF analysis of proteins to quickly search proteins as potential targets for drugs and biomarkers for disease on a proteome-wide scale. Additionally, it makes the unknown protein analysis of both qualitation and quantitation difficult because of off-line steps involved. Multi-step off-line processes of digestion, purification and concentration can result in significant loss of digested fragments or low recovery, thereby reducing the effectiveness of the overall process.

There remains a need to perform analytical and diagnostic assays for proteins and other biopolymers where the biopolymers are digested and biopolymer fragments are collected, separated or detected.

SUMMARY

Some embodiments of the present invention relate to methods for digesting a biopolymer in a medium. The medium is disposed adjacent a wall of a hollow element wherein at least a portion of the wall is porous and then exposed to digestion conditions to cleave the biopolymer into fragments. The fragments are permitted to permeate through the wall of the hollow element.

Some embodiments of the present invention are directed to methods for digesting a biopolymer in a medium wherein the medium is disposed on an exterior surface of a porous wall of a hollow element comprising a wall with an exterior surface and an interior surface defining an interior region. At least a portion of the wall is porous. The medium is exposed to digestion conditions to cleave the biopolymer into fragments, and the fragments permeate through the wall of the hollow element from the exterior surface to the interior region. The digestion conditions comprise a digestion agent on the exterior surface of the hollow element. The hollow element is disposed in the interior of a hollow liner.

Some embodiments of the present invention are directed to methods for analyzing a polypeptide sample. A medium comprising the polypeptide sample is introduced into a digestion region of a digestion device comprising a hollow element disposed parallel axially, for example, coaxially, in a nonporous hollow liner to provide the digestion region. The hollow element comprises a wall having an exterior surface and an interior surface defining an interior region. At least a portion of the wall is porous and at least a portion of the exterior surface has a polypeptide digestion agent immobilized thereon. The medium in the digestion region is subjected to digestion conditions to cleave the polypeptide into a mixture of fragments. The mixture of fragments permeates through the wall of the hollow element from the exterior surface to the interior region and is removed from the interior region. At least one of the fragments in the mixture are separated or detected or separated and detected.

Some embodiments of the present invention are directed to apparatus for analyzing a polypeptide sample. The apparatus comprises a digestion device comprising a hollow element disposed parallel axially, for example, coaxially, in a nonporous hollow liner to provide a digestion region wherein the hollow element comprises a wall having an exterior surface and an interior surface defining an interior region and wherein at least a portion of the wall is porous and at least a portion of the exterior surface has a polypeptide digestion agent immobilized thereon. In some embodiments the apparatus includes a polypeptide fragment separation device in fluid communication with the digestion device. In some embodiments the apparatus includes a polypeptide fragment detecting device in fluid communication with the separation device. In some embodiments the apparatus includes a trapping device for trapping the mixture of polypeptide fragments.

BRIEF DESCRIPTION OF THE DRAWINGS

The following figure is included to better illustrate the embodiments of the apparatus and techniques of the present invention. The figure is not to scale and some features may be exaggerated for the purpose of illustrating certain aspects or embodiments of the present invention.

DETAILED DESCRIPTION OF EMBODIMENTS OF THE INVENTION

Figure 1:
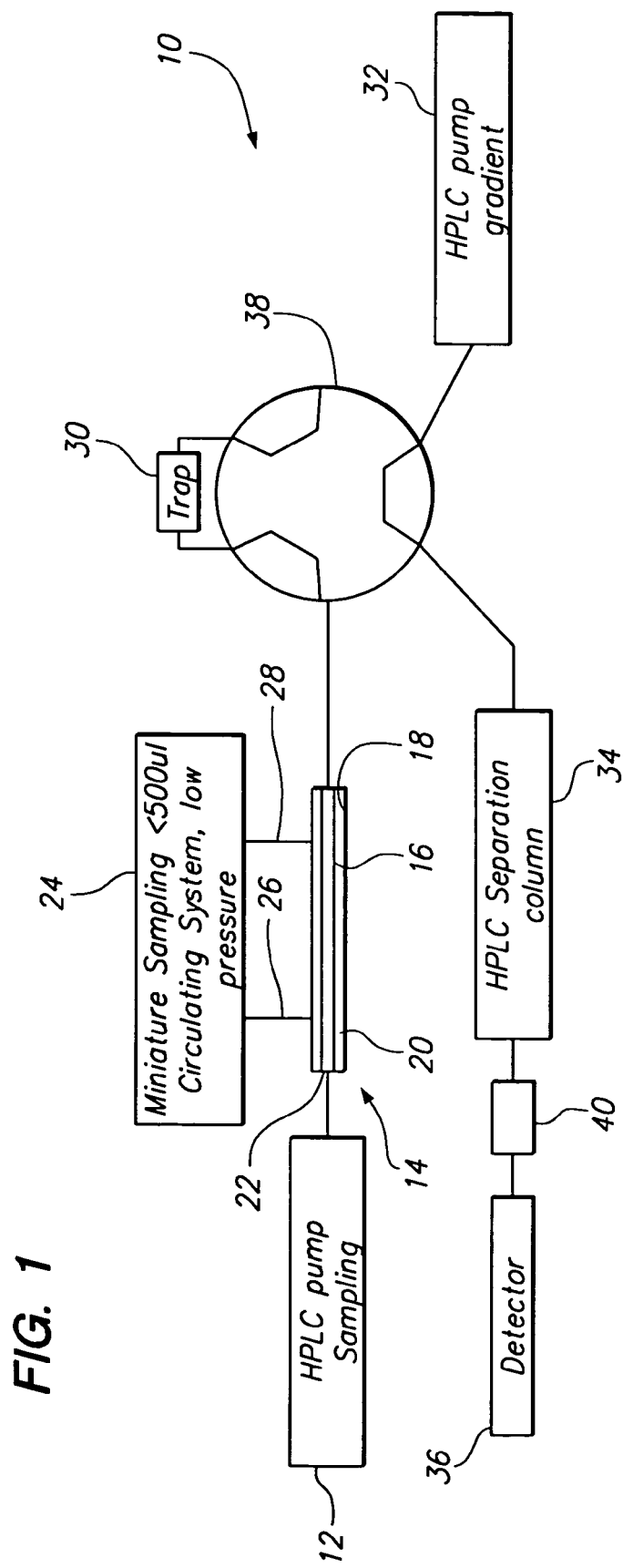
FIG. 1 is a schematic depicting an exemplary embodiment of an apparatus in accordance with the present invention.

Aspects of the present invention are directed to apparatus and methods for digesting a polymer such as, for example, a biopolymer, for example, a polypeptide, in a medium. Embodiments of the invention are directed to an on-line enzymatic digestion device, which may be a micro-reactor, for carrying out enzymatic digestions. The micro-reactor may be in communication with a trapping mechanism for trapping fragments produced by the enzymatic digestion of a polymer such as a biopolymer. In some embodiments the apparatus also includes a device for separating biopolymer fragments. In some embodiments the apparatus includes a device for detecting biopolymer fragments.

The term "biopolymer" refers to a polymer of one or more types of repeating units. Biopolymers are typically found in biological systems and particularly include polysaccharides (such as carbohydrates), and polypeptides (which term is used to include proteins whether or not attached to a polysaccharide) and polynucleotides as well as their analogs such as those compounds composed of or containing amino acid analogs or non-amino acid groups, or nucleotide analogs or non-nucleotide groups.

As used herein, a "polypeptide" refers to a biopolymer that comprises more than 20 consecutive amino acids. The term "polypeptide" encompasses proteins, fragments of proteins, cleaved forms of proteins, partially digested proteins, and the like, which are greater than about 20 consecutive amino acids.

As used herein a "peptide" refers to a biomolecule comprising fewer than about 20 consecutive amino acids.

As used herein, a "polynucleotide" refers to a biopolymer that comprises more than about 100 consecutive nucleotides or modified nucleotides. Polynucleotides include DNA, RNA, m-RNA, r-RNA, t-RNA, cDNA, DNA-RNA duplexes, etc.

As used herein, "oligonucleotide" refers to a biomolecule comprising fewer than about 100 nucleotides or modified nucleotides.

As used herein, a "polysaccharide" refers to a biopolymer that comprises more than about 10 consecutive saccharides or modified saccharides.

As used herein, "oligosaccharide" refers to a biomolecule comprising fewer than about 10 saccharides or modified saccharides.

Embodiments of Detection Devices

The digestion devices of the present invention are on-line. This means that the digestion device is in fluid communication with other components for separating and analyzing fragments of a polymer such as, for example, a biopolymer. The polymer fragments produced by the digestion are communicated on line to one of the other components such as, for example, to a trapping mechanism, to a separating mechanism and/or to a detecting mechanism. This is in direct contrast to carrying out the digestion off-line and manually taking the digestion fragments for purification (such as desalting) and concentration and then introducing them into a separation device and/or a detecting device such as, for example, HPLC, 2-dimensional LC (2D-LC), HPLC-MS, LC-MS, or tandem MS.

In some embodiments the digestion device comprises a hollow element disposed in a non-porous hollow liner to provide a digestion region wherein the hollow element comprises a wall having an exterior surface and an interior surface defining an interior region and wherein at least a portion of the wall is porous and at least a portion of the exterior surface has a polypeptide digestion agent immobilized thereon. By the phrase "at least a portion" means that the entire wall surface need not be porous but sufficient wall surface should be porous to achieve the desired separation of fragments from the biopolymer mixture.

Embodiments of the Hollow Element: The hollow element comprises an inner surface and an outer surface and should comprise at least a portion that is porous. One consideration is having a porous region that provides meaningful separation of peptide fragments of interest from larger molecules that are not of interest in a particular analysis. Usually, at least about 30%, at least about 50%, at least about 80%, or at least about 90%, or at least about 99%, or the entire hollow element is porous. The phrase "at least about" means that the porous region of the wall is equal to or greater than the designated percentage and that the designated percentage may vary by plus or minus one percent. The size of the pores should be sufficient to permit peptide fragments to pass through the device from the inner surface to the outer surface and to prevent undigested polypeptide from passing through the pores. The size of pores of the hollow element is about 1,000 molecular weight (MW) cutoff to about 10 microns, about 5,000 MW cutoff to about 5 microns, about 0.005 to about 4 microns, or about 0.01 to about 3 microns. The internal diameter of the hollow element is about 5 to about 2,000 microns, about 10 to about 1,000 microns, about 10 to about 700 microns, or about 20 to about 500 microns.

The hollow element can be manufactured from a number of materials. The hollow element should have sufficient integrity to withstand the separation conditions of the present method. The material from which the hollow element is constructed should be compatible with the polypeptide, the polypeptide fragments, the digestion medium including the digestion agent and any other ancillary materials such as, for example, digestion buffers, reducing agents and the like. The materials may be synthetic or natural or a combination of both. Materials include polymers, plastics including, e.g., polyesters, polyamides, etc., resins, polysaccharides such as, e.g., cellulose, cellulose esters such as nitrocellulose and the like, silica or silica-based materials, ceramics, clay/earth, carbon, metals including metal alloys, metal oxides, inorganic glasses, and so forth. Particular plastics finding use include, for example, polyethylene (PE), polypropylene (PP), such as high density polypropylene, polytetrafluoroethylene (PTFE), e.g., TEFLON®, polyethersulfone, PVDF, polymethylmethacrylate, polycarbonate, polyethylene terephthalate, polystyrene or styrene copolymers, polyurethanes, polyesters, polycarbonates, polyureas, polyamides, polyethyleneamines, polyarylene sulfides, polysiloxanes, polydimethylsiloxanes, polyimides, polyacetates, poly etheretherketone (PEEK), and the like. Metals include, for example, stainless steel, hastalloy, platinum, gold, silver, titanium, and so forth.

The shape of the hollow element may be, for example, circular, square, rectangular, elliptical, triangular, pentagonal, hexagonal and the like when viewed in the cross-section. In some embodiments the hollow element is tubular. In some embodiments the hollow element is a cylindrical device. The hollow element may be straight or curved, usually straight. For a curved element the angle of curvature is about 1 to about 90 degrees from an axis projected from the plane at one end of the element. The shape of the element is usually a matter of design and mechanical considerations.

The dimensions of hollow element may vary over the cross-section of the element from one point to another. For example, the cross-sectional dimension adjacent one end of the hollow element may be less than that adjacent the other end of such element. This configuration results in a tapered hollow element. On the other hand, for example, the cross-sectional dimensions at the ends of the element may be larger or smaller than the cross-sectional dimensions at the middle of the element. In general, the inner cross-sectional dimensions of the hollow element vary no more than about 80%, no more than about 50%, no more than about 30%, no more than about 20%, no more than about 10%, no more than about 5%, from one point to another along the length of the element. In many embodiments the inner cross-sectional dimension of the hollow element does not vary to any significant degree, i.e., no more than about 1%.

The length of the hollow element is dependent on a number of considerations. The length is usually based on the convenience of providing the hollow element as part of a digestion device that is on-line with other components of an apparatus as discussed below. The length is also dependent on providing an adequate digestion region as discussed below. In some embodiments the length of the hollow element is about 0.1 mm to about 10,000 mm, about 0.5 mm to about 1,000 mm or about 1 to about 500 mm. Conveniently, the length of the hollow element may be selected based on the commercially available products.

The thickness of the wall of the hollow element is dependent on a number of factors. One consideration is achieving an adequate separation of the peptide fragments from larger molecules. Another consideration is the structural or mechanical integrity or stability of the hollow element. The thickness of the wall of the hollow element is about 1 to about 10,000 microns, about 5 to about 5,000 microns, about 5 to about 1,000 microns, about 10 to about 1,000 microns, about 30 to about 600 microns, and so forth.

In a specific embodiment the hollow element is a hollow fiber membrane. The term "hollow fiber membrane" means an extremely small tube or fiber having an internal diameter of between about 5 to about 2,000 microns, about 10 to about 1,000 microns, about 10 to about 700 microns, or about 20 to about 500 microns. The outer diameter of the hollow fiber membrane depends on the internal diameter of the membrane and is generally less than about 3000 microns, less than about 2000 microns, or less than about 1000 microns. The hollow fiber membrane is constructed of any material suitable for hollow fiber membranes such as, for example, polyethylene, polyethersulfone, PVDF, and the like. The particular material chosen is dependent on the nature of the digestion agent, the digestion conditions, the nature of the polypeptides and/or fragments of polypeptides, and so forth. The hollow fiber membrane is operated in an "outside-in" mode wherein smaller polypeptide fragments produced by the digestion permeate through the pores of the hollow fiber, exit the interior wall, and pass into the interior of the hollow fiber. Larger polypeptide or larger polypeptide fragments from incomplete digestion do not pass through the hollow fiber membrane. An effluent comprising the polypeptide fragments of interest is formed in the interior of the hollow fiber and can flow through the internal bore of the hollow fiber membrane. The hollow fiber membrane should be chosen with a pore size sufficient to realize the aforementioned separation. The pore size of the hollow fiber membrane is about 1,000 MW cutoff to about 10 microns, about 1,000 MW cutoff to about 5 microns, about 1,000 MW cutoff to about 4 microns, or about 1,000 MW cutoff to about 3 microns. The wall thickness of the hollow fiber membrane is about 1 to about 1,000 microns, about 5 to about 1,000 microns, about 10 to about 1,000 microns. Suitable hollow fiber membranes include, by way of illustration and not limitation, PES, PVDF, PP, PE, and the like.

Embodiments of the Hollow Liner: As mentioned above, the digestion device comprises a hollow element disposed in a non-porous hollow liner to provide a digestion region. In many embodiments the hollow liner has two ends. Each of the two ends has at least two independent fluid communication ports. One of the fluid communication ports at each end is connected to the beginning of the interior of the hollow element. At least one of the fluid communication ports is connected to the gap region at a position preferably close to the corresponding end of the hollow liner.

In some embodiments the hollow element is disposed parallel axially in the hollow liner. The phrase "parallel axially" means that the cylindrical axis of the hollow element follows the contour of the cylindrical axis of the hollow liner. In some embodiments the cylindrical axis of the hollow element is parallel to the cylindrical axis of the hollow liner. A specific embodiment of parallel axially is coaxially where the cylindrical axes are the same for the hollow element and the hollow liner. In some embodiments, alignment of the axes may vary from coaxial by no more than about 50%, by no more than about 40%, by no more than about 30%, by no more than about 20%, by no more than about 15%, by no more than about 10% by no more than about 5%, or by no more than about 1%. The term "non-porous" means that fluid in the interior of the hollow liner is not able to pass through the wall of the hollow liner to any significant degree.

The hollow element is disposed within the hollow liner. The shapes of the hollow element and the hollow liner are generally the same but need not be. The shape and axial alignment of each should allow the formation of a digestion region between an inner wall of the hollow liner and an outer wall of the hollow element. The dimensions of the digestion region should be sufficient to permit the desired digestion reaction to be carried out in the digestion region. One or more hollow elements may be disposed within the hollow liner. For example, a hollow fiber bundle may be employed as the hollow element. The hollow elements are disposed such that each interior region of the hollow element would be in fluid communication with a single conduit that would receive the digestion effluent and provide a means to communicate the digestion fluid to a component of an analysis apparatus as discussed below. Alternatively, each interior region of the hollow elements separately communicates with such a component. In these embodiments, the outer surfaces of the hollow elements and the inner wall of the hollow liner form the digestion region.

The thickness of the wall of the hollow liner is dependent on a number of factors. One consideration is the structural or mechanical integrity or stability of the hollow liner, which must be sufficiently thick to maintain the integrity of the digestion region during the digestion process. Structural integrity is also related to the nature of the material from which the hollow liner is manufactured. The thickness of the wall of the hollow liner is about 100 to about 10,000 microns, about 200 to about 5,000 microns, about 200 to about 3,000 microns, about 200 to about 1,000 microns.

The hollow liner can be manufactured from a number of materials. Many of the considerations that apply to construction material for the hollow element mentioned above apply equally to the hollow liner.

The inner dimensions of the hollow liner are sufficient to permit the hollow element to be disposed therein and to permit the formation of the desired digestion region. The hollow liner accordingly has an inner cross-sectional dimension that accommodates the hollow element. The distance between the outer wall of the hollow element and the inner wall of the hollow liner element defines the digestion region. In general, this distance is related to volume of the digestion region needed for adequately carrying out the digestion reactions. In many instances the distance between the above walls is about 1 to about 5,000 microns, about 5 to about 1,000 microns, or about 10 to about 500 microns. The length of the hollow liner is sufficient to contain the hollow element, but it can extend outward of the hollow element to permit convenient flow connections and the like. Usually, the length of the hollow liner is co-terminal with the length of the hollow element. The hollow element is disposed within the hollow liner in such a way as to avoid any contamination of the digestion effluent that passes into the interior of the hollow element by the digestion medium in the digestion region.

In some embodiments both end sections of the hollow element are pot-sealed, for example, by adhesive within the hollow liner to form the digestion region and the interior of the hollow element where no fluid communication can occur between the two except through the pores of the hollow element. The hollow element and the hollow liner may be positioned with respect to each other by suitable spacers such as spacing rods, strips, posts and the like, O-rings, and so forth, made of ceramic, glass, polyimide, Teflon®, rubber, adhesive, and the like.

Embodiments of Detection Devices with Packing Material: The hollow element may contain a packing material inside the hollow element. The packing material may be disposed within the interior of the hollow element and into the porous region of hollow fiber wall. The purpose of the packing material is to retain the peptide fragments within the interior of the hollow element, to reduce permeation of digested polypeptide fragments through the porous wall of the hollow element, to block the permeation of the fragments through the porous wall of the hollow element, to modify surface property of the interior surface including surface dipole effect, hydrophobicity or hydrophilicity and the like. The packing material should have the characteristics of being surface porous, intrinsic porous, or non-porous. The packing material may have a surface modification with a different chemical entity from that of the body of the material. Such surface modifications include, by way of illustration and not limitation, C18, C8, or C4 polymer, and the like. In some embodiments the packing material has a particle size suitable to pack into either the interior region of the hollow element or the porous wall.

Suitable packing materials, by way of illustration and not limitation, include silica particles, dendrimers, divinylbenzene base polymers or copolymers thereof, metal oxides of metals such as, for example, zirconia, titania, alumina, and the like, crosslinked dextrins, gels, and so forth. The amount of packing material is usually sufficient to pack or fill the digestion region, i.e., porous wall volume or the interior of the hollow element over digestion length by about 10% to about 90%, about 10% to about 70%, about 10% to about 50%. The percentage of the packed material is defined as the volume of packing material over the open volume of the digestion region of the hollow element. In the case of the wall packing, the open volume is the porous volume of the wall over the digestion length, for an example, if the porosity of the wall is 30%, the volume of the wall over the digestion region is $V_w$, then the open volume of the digestion region is $0.3V_w$. In the case of the interior packing, if $V_0$ is the volume of interior region of the hollow element over the digestion length, then the open volume of the digestion region is $V_0$. The volume of the packing material is defined as the weight amount divided by the density of the packing material.

The size of the packing material is dependent on the nature of the packing material, the nature of the fluid medium, the nature of the digestion fragments, permeation rate, and so forth. The size of the packing material in cross-sectional dimension is about 0.01 to about 500 microns, about 0.01 to about 300 microns, about 0.01 to about 100 microns, about 0.01 to about 50 microns, about 0.01 to about 25 microns, and so forth.

Alternate Embodiments of Component Movement: The discussion above is primarily directed to embodiments wherein the digestion device formed by the hollow element disposed in the hollow liner is configured or adapted so that the mixture of fragments are permitted to permeate through the wall of the hollow element from the exterior surface to the interior region (outside-in) and then, if desired, may be passed out of the interior to another component of an analytic apparatus. However, in some embodiments the digestion device may be configured or adapted so that the mixture of fragments are permitted to permeate through the wall of the hollow element from the interior region to the gap region (inside-out) and then, if desired, may be passed out of the gap region to another component of an analytic apparatus. In these latter embodiments, a biopolymer digestion agent may be immobilized on the interior surface of the hollow element. Furthermore, connectors, ports and so forth are configured to adapt the digestion device to these latter embodiments.

Embodiments of Digestion Agents: As mentioned above, the outer surface of the hollow element comprises a reagent such as a digestion agent. The term "reagent" means a chemical species or combination of species essentially the sole purpose of which is to react chemically, directly or indirectly, with a sample species of interest to produce products from the sample species of interest. The digestion agent is a reagent that promotes the cleavage between bonds in the biopolymer to produce fragments of interest. The nature of the digestion agent is dependent on the nature of the biopolymer.

The digestion agent may be a small molecule (molecular weight less than about 2000, or less than about 1500, or less than about 1000) or a large molecule (molecular weight greater than about 2000, or greater than about 5000, or greater than about 10,000). The digestion agent may be immobilized reversibly or irreversibly on the outer surface of the hollow element. By "irreversibly immobilized" is meant that the digestion agent is attached to the outer surface of the hollow element in a manner that it is not significantly detached under the digestion conditions. Small molecule digestion agents are generally irreversibly immobilized on the outer surface of the hollow element so that these agents do not pass through the hollow element with the digestion effluent. Irreversible immobilization may be realized by covalent linkage of the digestion agent to the hollow element. To that end the hollow element is treated to introduce one or more functional groups on its surface for chemical reaction with one or more functional groups of the digestion agent. Large molecule digestion agents may be immobilized irreversibly or reversibly. In many embodiments the large molecule digestion agents are immobilized irreversibly as discussed above so that they remain attached and stable during the digestion process. In other embodiments the large molecule digestion agents are immobilized reversibly, which usually involves non-covalent interactions between the outer surface of the hollow element and the digestion agent. Such non-covalent interactions include, for example, adherence, absorption, adsorption, affinity attachment/hinge, immuno-hinge, and so forth.

Covalent attachment may be direct (such as by a bond between the digestion agent and the outer surface of the hollow element) or indirect (such as by a linking group between the digestion agent and the outer surface of the hollow element). Covalent or non-covalent attachment can be accomplished by well-known techniques, commonly available in the literature.

Examples of small molecule digestion agents, by way of illustration and not limitation, include cyanogen bromide, dimethyl sulfoxide/hydrobromic acid, dithiothreitol and the like. Examples of large molecule digestion agents, by way of illustration and not limitation, include enzymes, and the like. Enzyme cleaving agents for polypeptides, polynucleotides and polysaccharides are well-known in the art.

Enzymes may be immobilized on the hollow element by methods known in the art. See, for example, "Immobilized Enzymes," Ichiro Chibata, Halsted Press, New York (1978) and Cuatrecasas, J. Biol. Chem., 245:3059 (1970). A wide variety of functional groups are available or can be incorporated. Functional groups include carboxylic acids, aldehydes, amino groups, cyano groups, ethylene groups, hydroxyl groups, mercapto groups, and the like. Common examples of covalent immobilization include direct covalent attachment of an enzyme, for example, a protease, to an alkylamine-activated surface with ligands such as glutaraldehyde, isothiocyanate, and cyanogen bromide. However, proteases also can be immobilized on a solid phase using binding partners which specifically react with the proteases or which bind to or react with molecules which are themselves coupled to the proteases (e.g., covalently). Binding partners preferably have affinity constants greater than about $10^8$ or a dissociation constant of about $10^{-8}$. Representative examples of suitable ligand binding pairs include cytostatin/papain, valphosphanate/carboxypeptidase A, biotin/streptavidin, riboflavin/riboflavin binding protein, and antigen/antibody binding pairs. Preferably, the binding pair or molecule bound to the binding pair is positioned away from the catalytic site of the protease and/or other enzyme.

Examples of enzyme digestion agents for polypeptides include, by way of illustration and not limitation, proteases, and the like. Suitable proteases include, but are not limited to papain, trypsin, peptidases, such as, for example, aminopeptidases, carboxypeptidases, and endopeptidases (e.g., trypsin, chymotrypsin, thermolysin, endoproteinase Lys C, endoproteinase GluC, endoproteinase ArgC, endoproteinase AspN). Aminopeptidases and carboxypeptidases are useful in characterizing post-translational modifications and processing events. Combinations of proteases also can be used. Agents for sequence-specific cleavage also can be provided such as denaturing agents, for example, urea, guanidine, etc., reduction agents, for example, DTT (1,1bis(p-chlorophenyl)-2,2, 2-trichloroethane), etc., beta mercaptans, and the like.

Embodiments of Digestion Media: In many embodiments, the digestion agent utilizes a digestion medium, which is usually an aqueous medium and which may contain one or more buffers and other agents for assisting in bringing about digestion of the biopolymer. As a general rule, the digestion medium and conditions are chosen to maximize digestion and to avoid to any significant degree adverse affects on the digestion agent, the biopolymer to be digested, surface compatibility with digestion region materials (the hollow liner and hollow element and so forth. An aqueous medium may be solely water or may include from 0.01 to 80 or more volume percent of a cosolvent such as an organic solvent, for example, an alcohol, an ether, an amide, and the like. It will be understood that different enzymes break down proteins in different ways, i.e., at different points along the polypeptide chains, and at different rates, and some preliminary routine trials may be desirable to determine the best digestion enzyme and digestion conditions (e.g. pH, time, ionic strength, temperature) in any particular case.

The pH for the medium depends on such factors as the nature of the digestion agent, the nature of the polypeptides and fragments of polypeptides, and so forth. The pH will usually be in the range of about 4 to 13, in the range of about 5 to 10, in the range of about 6.5 to 9.5. The pH is generally selected to achieve optimum biopolymer digestion.

Various buffers may be used to achieve the desired pH and maintain the pH during the digestion. Illustrative buffers include borate, phosphate, carbonate, tris, barbital and the like. The particular buffer employed is not critical to this invention, but in an individual digestion one or another buffer may be preferred. Various ancillary materials may be employed in the method in accordance with the present invention. For example, in addition to buffers the medium may comprise stabilizers for the medium and for the reagents employed.

The medium is usually incubated at a temperature and for a time sufficient for digestion of the biopolymers to occur so that the fragments can be separated and detected. Moderate temperatures are normally employed for carrying out the method and usually constant temperature; however, under certain circumstances it may be desirable to use more than one temperature during the digestion. Suitable temperatures normally range from about 5° to about 99° C., from about 15° C. to about 70° C., from about 20° C. to about 45° C. The time period for the incubation is dependent on, for example, the kinetics of the reactions between the digestion agent(s) and the biopolymers, and so forth and is about 0.2 seconds to about 12 hours, about 2 seconds to 1 hour, about 10 to about 30 minutes. The time period depends on, among others, the temperature of the medium, the concentration of the digestion agent(s) and the like.

The amount of biopolymer will generally vary from about 1 to about 100,000 nanograms (ng), about 0.1 to about 10 micrograms, about 0.1 to about 100 micrograms.

In some embodiments of the present invention such as, for example, where the hollow element has a large number of pores as in a hollow fiber, the amount of enzyme immobilized on the outer surface of the hollow element can be high. For example, in some embodiments the number of enzyme molecules to the number of protein molecules may be about 50 to about 1, about 40 to about 1, about 30 to about 1, about 20 to about 1, about 10 to about 1, or about 5 to about 1. Such high ratios may be utilized because of embodiments of the present invention employing a high porosity hollow element such as a hollow fiber. In other embodiments the enzyme to protein molecular ratio is about 4 to about 1, about 3 to about 1, about 2 to about 1, about 1 to about 1, about 1 to about 2, about 1 to about 3, about 1 to about 4, about 1 to about 5, about 1 to about 10, or the like. The amount of enzyme should be sufficient to achieve effective digestion of the protein in a reasonable period of time.

Surface Modifications of the Hollow Element: Some components of the digestion medium such as salts, buffers, and the like do not permeate through the hollow element because of modification of the outer surface of the hollow element and the hydrophobicity of the flow media inside the hollow element. The outer surface of the hollow element may be modified by a surface modification such as, for example, a surface coating with a suitable polymer such as, e.g., polyvinylpyrrolidone, polyvinyl alcohol, and the like, or by radiation to produce an oxide surface. In some embodiments the hydrophobicity of the flow media in the interior of the hollow element may be achieved by the virgin surface of the hollow element material, i.e., aliphatic hydrocarbons or other groups.

Digestion Region and Sampling System: The digestion region is in fluid communication with a sampling system to provide a sample to be digested. The sampling system operates under low pressure of about 0.05 to about 150 psi, about 0.05 to about 100 psi, about 0.1 to about 60 psi, or the like. Fluid communication between the sampling system and the digestion region is established by means of appropriate fluid connectors to one or more ports in the hollow liner. The ports serve as inlets or outlets as necessary to achieve fluid communication between the sampling system and the digestion region. The sampling system may be a HPLC sampling valve, syringe, solenoid valve, pump, or the like. The volume of the sampling system is dependent on the amount of polypeptide solution and the workable wash volume, and so forth. The volume of sampling system may be about 5 to about 20,000 microliters, about 10 to about 10,000 microliters, about 20 to about 5,000 microliters, about 50 to about 1,000 microliters, about 100 to about 800 microliters, about 200 to about 700 microliters, or about 300 to about 600 microliters.

Digestion Region and Analytic Components: The digestion device formed by the hollow element disposed in the hollow liner is configured or adapted so that the digestion effluent (comprising the digested biopolymer fragments) in the interior of the hollow element may be passed out of the interior to another component of an analytic apparatus. Accordingly, the hollow element has at least one port for providing fluid communication between the interior of the hollow element and such a component. Furthermore, the hollow liner has one or more ports for introduction of biopolymer to be digested into the digestion region of the digestion device and for removal of spent materials from the digestion region. The phrase "at least one port" or "one or more ports" means that the number of ports may be one, two, three, four, and so forth.

Trapping of Digestion Fragments: Trapping of the digestion fragments may be accomplished by known techniques such as a capillary column packed with a suitable packing material such as, e.g., C18 particle, C8 particle, C4 particle, ion exchange resin, and the like, under suitable gradient flow of the mobile phase, and the like. Trapping of the fragments may also be achieved using another hollow fiber with surface modification that differs from that of the hollow element to product an osmosis effect in that outer region, and so forth.

Separation of the Digestion Fragments: The fragments may be separated using a separation device or technique such as, for example, chromatography using a suitable chromatographic material, the nature of which is dependent on the nature of the chromatography and is generally well-known in the art. Chromatography is a method of separating mixtures of compounds into their components. It enables one to separate trace impurities or major fractions from each other. These separated components can then be analyzed by various methods, including spectrographic methods.

Chromatography is based on the separation of different types of molecules as they pass along a chromatographic material usually confined in a housing such as a column. The housing may be packed with a material that provides a high surface area, e.g., packed column, or the material may be present as film coated on the walls of the internal walls of the housing, e.g., open tubular column. The packing or wall-coated film of inert material acts as a stationary phase. The chromatographic material is a material that exhibits attractive selectivity for certain compounds. The chromatographic material may interact physically with the compounds being analyzed. As a sample to be analyzed passes along the chromatographic material, it separates into its different components, which can then be characterized and identified. This approach can also be used to measure how much of each component is present in the mixture.

The chromatographic technique employed for separation of the fragments in some embodiments of the present invention may be liquid chromatography, including high performance liquid chromatography, liquid flow driven by a constant flow pump, gradient flow of mobile phase, and the like.

Detection of Digestion Fragments: Any suitable detector known in the art or otherwise available may be employed to detect the separated fragments and result in their identification. Examples of detectors include, by way of illustration and not limitation, mass spectrometer, Ultraviolet-visible spectrophotometer, immuno-based sensor, electron capture detector, thermal conductivity detector, and so forth, and combinations thereof. The present apparatus is adapted for connection to a detector, which may be realized employing connectors that are well-known in the art. The connection can be direct to the detector or indirect to the detector through an interface, which may be, for example, chip-LC, chip-nozzle, micro-machined fluidic channel, an external nozzle to MS, and the like.

Mass spectrometry is an analytical methodology used for quantitative chemical analysis of materials and mixtures of materials. In mass spectrometry, a sample of a material, usually an organic or inorganic or biomolecular sample, to be analyzed called an analyte is broken into electrically charged particles of its constituent parts in an ion source. The particles are typically molecular in size. Once produced, the analyte particles are separated by the spectrometer based on their respective mass-to-charge ratios. The separated particles are then detected and a mass spectrum of the material is produced. The mass spectrum is analogous to a fingerprint of the sample material being analyzed. The mass spectrum provides information about the masses and, in some cases, quantities of the various analyte ions that make up the sample. In particular, mass spectrometry can be used to determine the molecular weights of molecules and molecular fragments within an analyte. Additionally, to some extent mass spectrometry can identify molecular structure and sub-structure and components that form the structure within the analyte based on the fragmentation pattern when the material is broken into particles. Mass spectrometry has proven to be a very powerful analytical tool in material science, chemistry and biology along with a number of other related fields.

Mass spectrometers employing ionization chambers, such as atmospheric pressure chemical ionization (APCI) chambers, electrospray ionization chamber (ESI), surface enhanced laser desorption ionization (SELDI), and so forth, have been demonstrated to be particularly useful for obtaining mass spectra from liquid or gaseous samples and have widespread application. Mass spectrometry (MS) is frequently used in conjunction with gas chromatography (GC) or liquid chromatography (LC), and combined GC/MS and LC/MS systems are commonly used in the analysis of analytes having a wide range of polarities and molecular weights. Combined LC/MS systems have been particularly useful for applications such as environmental monitoring, pharmaceutical analysis, industrial process and quality control, and the like.

Liquid chromatography/mass spectrometry (LC/MS) analysis of protein enzymatic digests is an important technology with a wide variety of applications including protein sequencing, analysis of post-translational modifications, proteomics, quality control of therapeutic and other protein preparations, etc. Conventional methods usually involve electrospray (ESI) ionization of the effluent from a reversed phase high performance liquid chromatography (HPLC) separation followed by mass spectrometry with any of a variety of fragmentation techniques. Fragmentation caused by collisions within the ESI interface is often employed to generate sequence information. Tandem MS/MS using triple quadrupole or quadrupole time of flight instruments are often the method of choice for such analyses.

In some embodiments, for high throughput identification of polypeptides, matrix assisted laser-desorption ionization mass spectrometry (MS) peptide finger printing is one method of choice. Although this method is fast, it requires protein database matching and provides the least detailed information. When more detail is needed, ionization tandem mass spectrometry (ESI-MS/MS) is the method of choice (see, e.g., Karger et al., 1993, Anal Chem. 65: 900-906). MS/MS is capable of giving amino acid level sequence information and is used for de novo sequencing and analysis of post-translational modifications. The development of automated database searching programs to directly correlate MS/MS spectra with sequences in protein and nucleic acid databases has greatly increased throughput. Hybrid instruments combine MALDI with MS/MS.

In some embodiments the procedure for analysis by mass spectrometry of a single protein or a mixture of proteins comprises following steps: a) joint enzymatic digestion of all proteins in the protein mixture, b) separation of the peptides in the mixture by liquid chromatography, preferably into the highest resolution columns possible, c) the digestion peptides are ionized by matrix assisted laser desorption (MALDI), surface enhanced laser desorption (SELDI), ESI, or the like, the flight times of the ions are measured in the time-of-flight mass spectrometer, and from these flight times the masses of the digestion peptide ions are determined (the spectra generated are called digestion peptide spectra), and d) the associated proteins are identified by searching in protein sequence, EST, cDNA or DNA databases.

Embodiments of Methods of the Invention

As mentioned above, some embodiments of the present invention are directed to methods for digesting a polypeptide in a medium. The methods comprise disposing the medium on an exterior surface of a porous wall of a hollow element comprising a wall with an exterior surface and an interior surface defining an interior region. At least a portion of the wall is porous. The medium is exposed to digestion conditions to cleave the polypeptide into fragments, and the fragments permeate through the wall of the hollow element from the exterior surface to the interior region. Some embodiments of the present invention are directed to methods for analyzing a polypeptide sample. A medium comprising the polypeptide sample is subjected to digestion as described above. The fragments that have permeated through the wall of the hollow element are optionally trapped and then optionally separated from salt and other molecules not suitable for detection and subsequently optionally detected.

Materials to be Analyzed

The sample containing the biopolymer may be a body fluid or a non-body fluid. The phrase "body fluid" refers to any fluid obtained from the body of a mammal (e.g., human, monkey, mouse, rat, rabbit, dog, cat, sheep, cow, pig, and the like) that is suspected of containing a particular target protein or proteins to be detected. Body fluids include, for example, whole-blood, plasma, serum, interstitial fluid, sweat, saliva, urine, semen, blister fluid, inflammatory exudates, stool, sputum, cerebral spinal fluid, tears, mucus, and the like, collection fluids used to collect proteins from protein-containing materials such as biological tissue and the like, and so forth. The biological tissue includes excised tissue from an organ or other body part of a host.

The phrase "non-body fluid" refers to any fluid not obtained from the body of a mammal, which is suspected of containing a particular target protein or proteins to be detected. Exemplary non-body fluids include cell-culture media, dialysate, and the like. The protein sample can be examined directly or may be pretreated to fragment the protein into fragments for analysis.

A single protein may be analyzed or a mixture of proteins may be analyzed. For determining a mixture of proteins, one may use intact cells, intact viruses, viral infected cells, lysates, plasmids, mitochondria or other organelles, fractionated samples, or other aggregation of proteins, separated proteins, and treated proteins, by themselves or in conjunction with other compounds. Any source of a mixture of proteins can be used, where there is an interest in identifying a plurality of proteins. Protein analytes may be isolated using precipitation, extraction, and chromatography. The proteins may be present as individual proteins or combined in various aggregations, such as organelles, cells, viruses, etc. Protein analytes may be released from cells, for example, by lysing the cells.

One area of application of embodiments of the present invention is proteomics. A proteome is defined as the totality of all the proteins of one cell type under precisely defined boundary conditions. Because higher life forms contain several hundred types of cells, there are also hundreds of proteomes. At the same time, there are proteins that are common to all the cell types of a particular entity, and those that are specific to one type of cell. The proteome, moreover, is not unchangeable, being modified both qualitatively and quantitatively with boundary conditions such as age, or stress on the cell community resulting from the administration of medication.

Of special interest, of course, are the proteins of a proteome that are not yet known, both for their application as pharmaceutical target proteins and also as possible independent active substances, i.e., proteins suitable for pharmaceutical use. Also of great value for understanding the function of cell communities are those proteins whose quantity changes when the cell community is stressed, such as through age, the administration of medicine, or diseases.

It is estimated that mammals possess well over 100,000 proteins, whose structural plans are to be found in somewhere between 30,000 to 40,000 genes. There are estimates that indicate that from one gene alone, the process of "splicing" gives rise, as a statistical average, to about three and a half different types of protein. Furthermore, many more proteins are created through post-translational modifications. A proteome contains from some thousands up to some tens of thousands of proteins. Not even half the human proteins are known today.

Other areas of application of embodiments of the present invention include, for example, protein sequencing, analysis of post-translational modifications, quality control of therapeutic and other protein preparations, preparation of antibodies or Affibody™ antibodies, toxicity studies, and the like.

Other areas of application of embodiments of the present invention include genomics, which may be described as the comprehensive analysis of DNA structure and function. Understanding biological diversity at the whole genome level will yield insight into the origins of individual traits and disease susceptibility. Though organisms such as humans are quite similar at the genetic level, differences exist at a frequency of about one in every 1000 nucleotide bases. This translates into approximately 3 million base differences between each individual. Such changes are referred to as single nucleotide polymorphisms (SNP's) and a significant effort is now underway in the research community to map the individual SNP's in humans and other organisms. SNP's may be found within gene coding regions or in non-coding regions. Their effects may be subtle yielding slight changes in protein function or profound, leading to the development of disease. A polymorphism is distinct from a mutation. The latter is considered rare, affecting less than one percent of the species, whereas a polymorphism is relatively common and its prevalence is no different to what is considered normal.

Another area of application of the present methods is the study and analysis of polysaccharides or carbohydrates as they relate to biological processes. Carbohydrates are the most abundant class of organic compounds found in living organisms. They originate as products of photosynthesis, an endothermic reductive condensation of carbon dioxide requiring light energy and the pigment chlorophyll. As noted here, the formulas of many carbohydrates can be written as carbon hydrates, $C_n(H_2O)_n$, hence their name. The carbohydrates are a major source of metabolic energy, both for plants and for animals that depend on plants for food. Aside from the sugars and starches that meet this vital nutritional role, carbohydrates also serve as a structural material (cellulose), a component of the energy transport compound ATP, recognition sites on cell surfaces, and one of three essential components of DNA and RNA.

Embodiments of Apparatus

Some embodiments of the present invention are directed to apparatus for analyzing a polypeptide sample. The apparatus comprises a digestion device comprising a hollow element disposed parallel axially, for example, coaxially, in a nonporous hollow liner to provide a digestion region wherein the hollow element comprises a wall having an exterior surface and an interior surface defining an interior region and wherein at least a portion of the wall is porous and at least a portion of the exterior surface has a polypeptide digestion agent immobilized thereon. In some embodiments the apparatus includes a polypeptide fragment separation device in fluid communication with the digestion device. In some embodiments the apparatus includes a polypeptide fragment detecting device in fluid communication with the separation device. In some embodiments the apparatus includes a trapping device for trapping the mixture of polypeptide fragments.

The apparatus also may include connections of the system, which may comprise one or more of pumps, valves, drainage lines for undesired flow through material, detector inlets and outlets, HPLC columns including chip-columns, other columns, fractionate collectors, and so forth.

The components of the present apparatus are adapted to perform a specified function usually by a combination of hardware and software. This includes the structure of the particular component and may also include a microprocessor, embedded real-time software and I/O interface electronics to control a sequence of operations and so forth.

One embodiment of an apparatus is depicted in FIG. 1. Apparatus 10 comprises a sampling HPLC pump 12 for providing mobile phase flow into region 22 of hollow fiber 16 to push the digested fragments into trap system 30, whereby the fragments are separated from undesired molecules such as salts or smaller fragments under well known mobile phase composition (such as high content of organic solvent in the mobile phase) driven by gradient pump 32. Pump 12 is in fluid communication with digestion device 14, which comprises hollow fiber 16 disposed within hollow liner 18 to form digestion chamber 20. Hollow fiber 16 is disposed within hollow liner 18 in a sealed manner so that the only communication that occurs between digestion region 20 and interior region 22 of hollow fiber 16 is through the pores of hollow fiber 16. Digestion region 20 is in fluid communication with a low pressure miniature sampling circulating system 24 through lines 26 and 28, which respectively serve as inlet and outlet ports in hollow liner 18 to digestion region 20. System 24 has a volume of about 500 microliters in this embodiment. The outer surface 16a of hollow fiber 16 is coated with an enzymatic digestion agent 17 such as, for example, trypsin in this embodiment. Interior region 22 is in fluid communication with trapping system 30, which in the embodiment depicted is a capillary column and is connected to digestion device 14 and gradient pump 32 through a switch valve 38. Gradient HPLC pump 32 is used to provide mobile phase flow to further separate digested fragments inside HPLC separation column 34 after these fragments are pushed out of trap system 30 and into separation device 30. Trapping system 30 is in fluid communication with separation device 34, which is a HPLC separation column in this embodiment. Detector 36 is in communication with separation device 34 through optional interface 40.

In operation, sampling HPLC pump 12 provides mobile phase flow into interior region 22 of hollow element 16. The flow may be about 0.001 ml/min to about 1 ml/min, about 0.001 ml/min to about 0.5 ml/min, about 0.001 ml/min to about 0.1 ml/min. The mobile phase wets the hollow element wall. A protein sample comprising the protein of interest in a digestion buffer is introduced into digestion region 20 through inlet line 28, either by switch valve or manual injection with a syringe. The digestion buffer containing the protein sample is circulated by device 24. The circulating flow rate is sufficiently slow to maintain an effective rate of digestion of the protein based on balancing permeation rate of the digested fragments and mobile phase flow from the pump 12. The flow rate for introduction of the sample medium into the digestion region is sufficient to maintain an effective rate of digestion of the protein. The flow rate may be constant or it may be varied during the process. In some embodiments the flow may be stopped periodically during the digestion. The rate of circulating flow is about 0.1 µl per minute to about 1 ml per minute, about 1 µl per minute to about 0.2 ml per minute, about 5 µl per minute to about 0.1 ml per minute. The protein sample circulates in digestion region 20 and the protein is digested into peptides that pass through the pores of hollow fiber 16 into interior region 22, where they are removed to trapping system 30 under direction of the flow from the pump 12. After all fragments are pushed into the trap 30, gradient HPLC pump 32 switches another mobile phase flow into the trap 30 to push the separated fragments into separation column 34. This mobile flow can be gradient, too for efficient separation of digested peptides. The separated peptides are then analyzed in detector 36 to determine their respective identities.

Results of Analysis

One aspect of embodiments of the invention is the product of the above method, namely, the results of a biopolymer analysis, which may be evaluated at the site of the testing or it may be shipped to another site for evaluation and communication to an interested party at a remote location if desired. By the term "remote location" is meant a location that is physically different than that at which the results are obtained. Accordingly, the results may be sent to a different room, a different building, a different part of city, a different city, and so forth. Usually, the remote location is at least about one mile, usually, at least ten miles, more usually about a hundred miles, or more from the location at which the results are obtained. The data may be transmitted by standard means such as, e.g., facsimile, mail, overnight delivery, e-mail, voice mail, and the like.

"Communicating" information references transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data.

As used herein, the phrase "at least" means that the indicated item is equal to or greater than that designated value and the term "about" means that the designated value may vary by plus or minus one percent.

All publications and patent applications cited in this specification are herein incorporated by reference as if each individual publication or patent application where specifically and individually indicated to be incorporated by reference.

Although embodiments of the foregoing invention have been described in some detail by way of illustration and example for purposes of clarity of understanding, it will be readily apparent to those of ordinary skill in the art in light of the teachings of this invention that changes and modifications may be made thereto without departing from the spirit or scope of the appended claims. Furthermore, the foregoing description, for purposes of explanation, used specific nomenclature to provide a thorough understanding of the invention. However, it will be appreciated that one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A method for digesting a biopolymer in a medium, said method comprising:
   (a) disposing a medium comprising a biopolymer adjacent an exterior surface of a wall of a hollow element defining an interior region, wherein at least a portion of the wall is porous and the hollow element is disposed in the interior of a hollow liner,
   (b) exposing the medium to a biopolymer digestion agent irreversibly immobilized on said exterior surface of the wall to cleave the biopolymer into fragments; and
   (c) permitting the fragments to permeate through the wall of the hollow element from said exterior surface to said interior region.

2. A method according to claim 1 wherein the hollow element is a hollow fiber.

3. A method according to claim 1 wherein said hollow element is disposed in the interior of a hollow liner.

4. A method according to claim 1 wherein the biopolymer digestion agent comprises one or more enzymes.

5. A method according to claim 1 further comprising removing the fragments from the interior region of the hollow element.

6. A method according to claim 1 wherein the hollow element is parallel axially disposed in the interior of the hollow liner.

7. A method for analyzing a polypeptide sample, said method comprising:
   (a) introducing a medium comprising the polypeptide sample into a digestion region of a digestion device comprising a hollow element disposed in a non-porous hollow liner to provide the digestion region wherein the hollow element comprises a wall having an exterior surface and an interior surface defining an interior region and wherein at least a portion of the wall is porous and at least a portion of the exterior surface has a polypeptide digestion agent irreversibly immobilized thereon,
   (b) subjecting the medium in the digestion region of the digestion device to the polypeptide digestion agent to cleave the polypeptide into a mixture of fragments,
   (c) permitting the mixture of fragments to permeate through the wall of the hollow element from the exterior surface to the interior region,
   (d) removing the mixture of fragments from the interior region,
   (e) separating the fragments in the mixture with a separation device, and
   (f) detecting at least one of the separated fragments with a detection device, wherein the digestion device, the separation device and the detection device are in fluid communication.

8. A method according to claim 7 wherein the hollow element is a hollow fiber.

9. A method according to claim 7 wherein the medium comprises a digestion buffer.

10. A method according to claim 7 wherein the polypeptide digestion agent comprises one or more enzymes.

11. A method according to claim 7 wherein the mixture of fragments from the interior region are removed by pumping.

12. A method according to claim 7 wherein the fragments in the mixture are separated by a chromatographic method.

13. A method according to claim 12 wherein the chromatographic method is liquid chromatography or high performance liquid chromatography or a combination thereof.

14. A method according to claim 7 wherein the separated fragments are detected by mass spectrometry, ultraviolet-visible spectrophotometry or immuno-based sensor technology or a combination thereof.

15. A method according to claim 7 wherein the hollow element is parallel axially disposed in the interior of the hollow liner.

* * * * *